US012735391B2

(12) United States Patent
Patel et al.

(10) Patent No.: US 12,735,391 B2
(45) Date of Patent: Sep. 15, 2026

(54) POLYMORPHS OF PONESIMOD

(71) Applicant: TAPI CZECH INDUSTRIES S.R.O., Opava-Komarov (CZ)

(72) Inventors: Rohit Dwarkabhai Patel, Greater Noida (IN); Vinod Ramesh Borase, Shahada (IN); Anantha Rajmohan Muthusamy, Sivakasi (IN); Amit Singh, Greater Noida (IN)

(73) Assignee: TAPI CZECH INDUSTRIES S.R.O., Opava-Komarov (CZ)

( * ) Notice: Subject to any disclaimer, the term of this patent is extended or adjusted under 35 U.S.C. 154(b) by 310 days.

(21) Appl. No.: 18/576,412

(22) PCT Filed: Aug. 9, 2022

(86) PCT No.: PCT/US2022/039770
§ 371 (c)(1),
(2) Date: Jan. 4, 2024

(87) PCT Pub. No.: WO2023/022896
PCT Pub. Date: Feb. 23, 2023

(65) Prior Publication Data

US 2024/0368094 A1 Nov. 7, 2024

(30) Foreign Application Priority Data

Aug. 17, 2021 (IN) ............................ 202111037253
Apr. 21, 2022 (IN) ............................ 202211023529

(51) Int. Cl.
*C07D 277/54* (2006.01)
*A61K 31/426* (2006.01)

(52) U.S. Cl.
CPC .......... *C07D 277/54* (2013.01); *A61K 31/426* (2013.01)

(58) Field of Classification Search
CPC ............................ C07D 277/54; A61K 31/426
USPC .......................................................... 514/369
See application file for complete search history.

(56) References Cited

U.S. PATENT DOCUMENTS 9,062,014 B2 6/2015 Bonham et al.
11,013,723 B1 5/2021 Huang et al.
2019/0345120 A1 11/2019 Chen et al.

FOREIGN PATENT DOCUMENTS

WO 2005054215 A1 6/2005
WO 2008062376 A2 5/2008
WO 2014027330 A1 2/2014
WO 2017107972 A1 6/2017
WO 2019060147 A1 3/2019

OTHER PUBLICATIONS

International Search Report and Written Opinion of the International Searching Authority issued in corresponding application PCT/US2022/039770 mailed Nov. 7, 2022 (17 pages).

*Primary Examiner* — Kristin A Vajda
(74) *Attorney, Agent, or Firm* — Carter, DeLuca & Farrell LLP

(57) ABSTRACT

The present disclosure encompasses Ponesimod crystalline forms, processes for preparation thereof, and pharmaceutical compositions thereof.

23 Claims, 2 Drawing Sheets

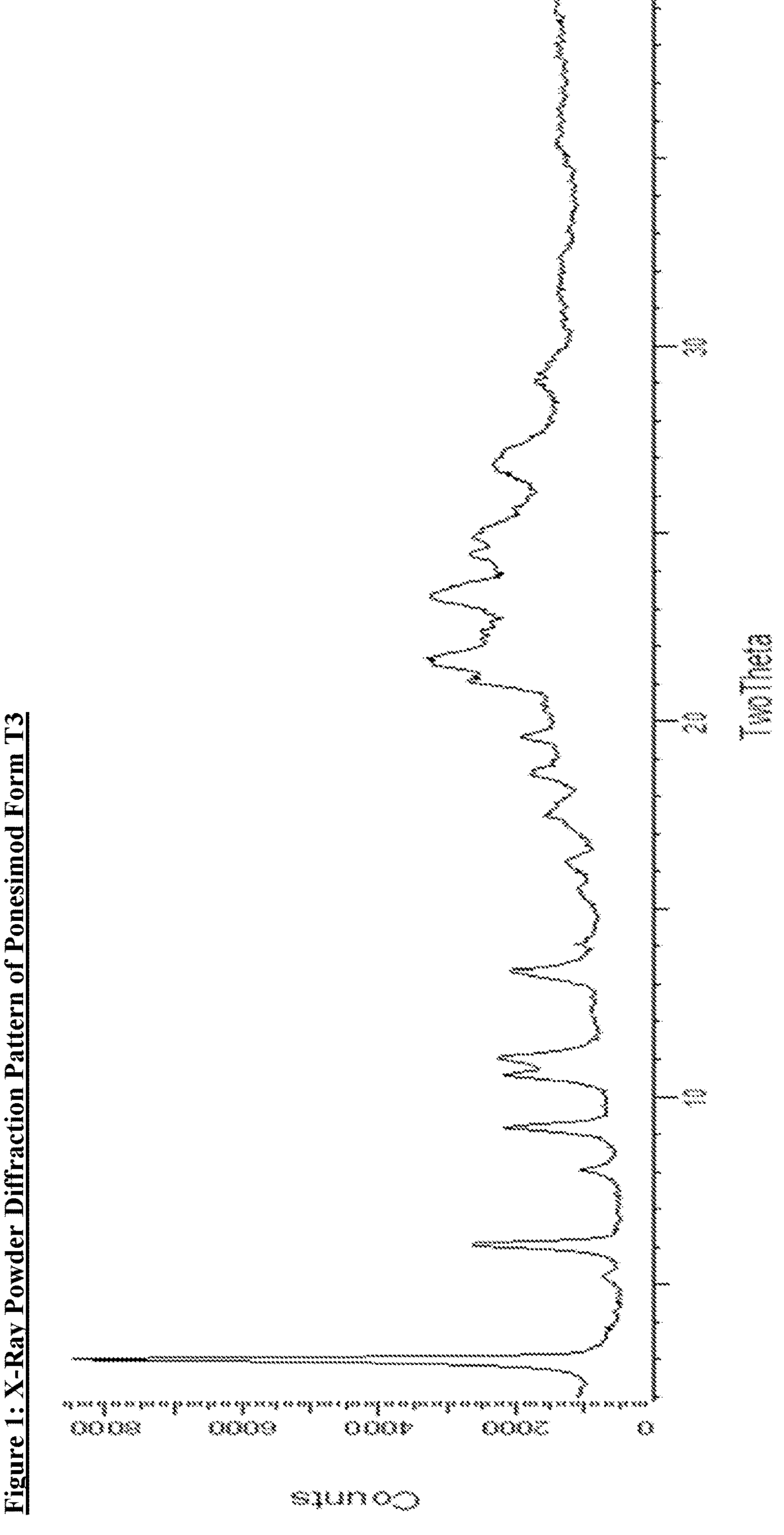
Figure 1: X-Ray Powder Diffraction Pattern of Ponesimod Form T3

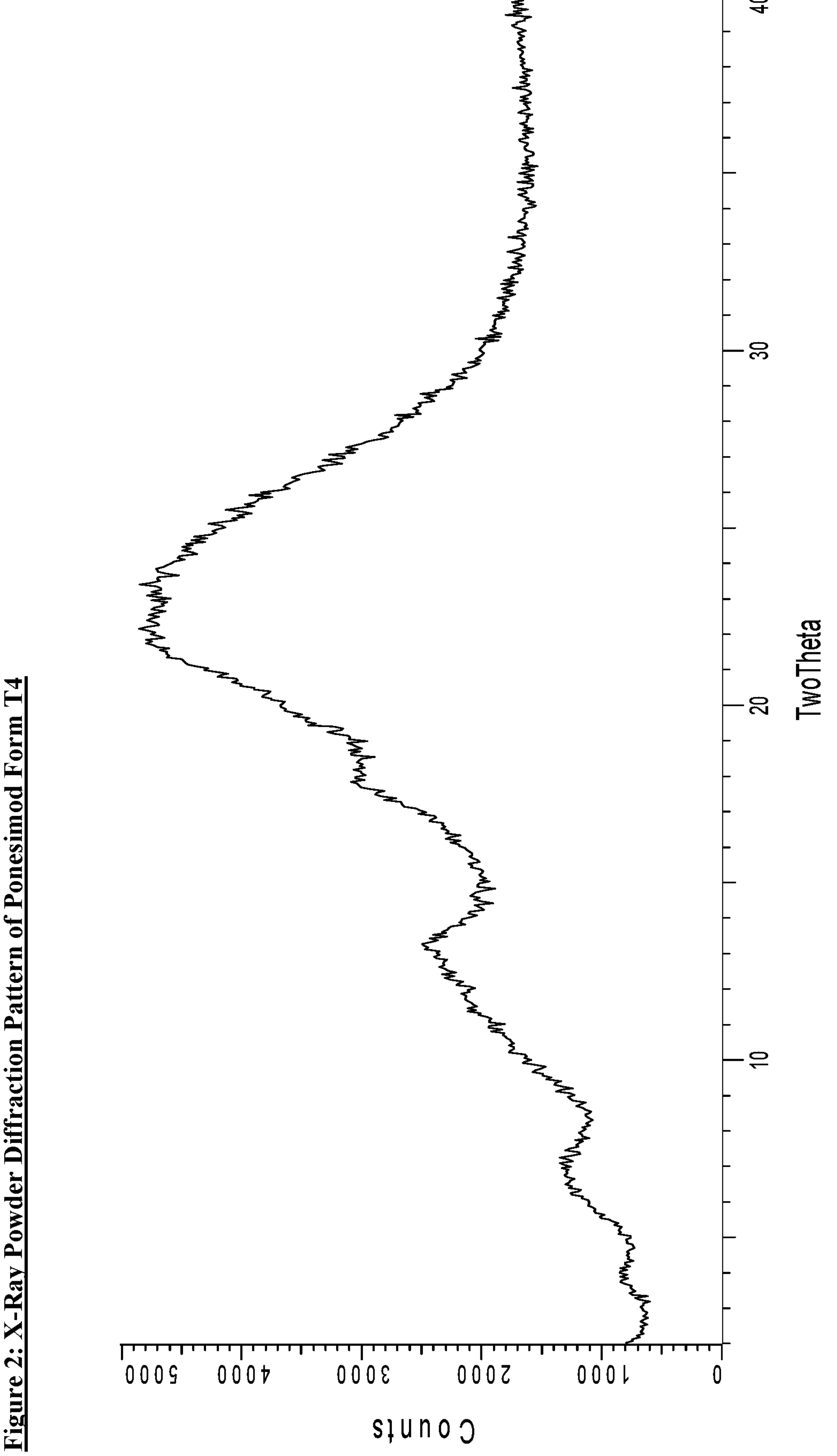
Figure 2: X-Ray Powder Diffraction Pattern of Ponesimod Form T4

POLYMORPHS OF PONESIMOD

CROSS REFERENCE TO RELATED APPLICATIONS

This application is a National Stage of, and claims priority to and the benefit of, International Patent Application No. PCT/US2022/039770, filed on Aug. 9, 2022, which, in turn, claims the benefit of and priority to, Indian Provisional Application No. 202111037253, filed on Aug. 17, 2021 and Indian Provisional Application No. 202211023529, filed on Apr. 21, 2022, the entire disclosures of each of which are incorporated by reference herein.

FIELD OF THE DISCLOSURE

The present disclosure encompasses solid state/crystalline forms of Ponesimod, processes for preparation thereof, and pharmaceutical compositions thereof.

BACKGROUND OF THE DISCLOSURE

Ponesimod has the chemical name (R)-5-[3-chloro-4-(2,3-dihydroxy-propoxy)-benz[Z]ylidene]-2-([Z]-propylimino)-3-o-tolyl-thiazolidin-4-one), and the following chemical structure:

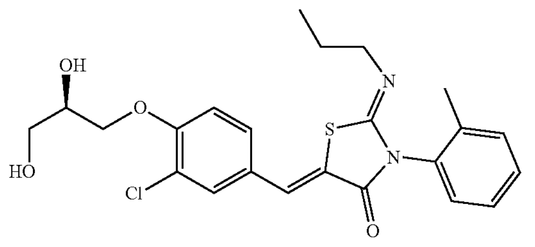 [SMILES: CCC/N=C1\S/C(=C\c2ccc(OC[C@H](O)CO)c(Cl)c2)C(=O)N1c1ccccc1C]

Ponesimod is a Sphingosine-1-phosphate receptor-1 ($S_1P_1$) agonist, under development for the treatment of certain pathologies, e.g.: autoimmune diseases, for example, multiple sclerosis (MS), such as relapsing MS, or relapse-remitting MS.

The compound is described in International Publication No. WO 2005/054215. A process for its preparation is described in International Publication No. WO 2008/062376, as well as in International Publication No. WO 2014/027330. International Publication Nos. WO 2010/046835 (U.S. Pat. No. 9,062,014), WO 2017/107972 and WO 2019/060147 describe crystalline forms of Ponesimod.

Polymorphism, the occurrence of different crystalline or solid state forms, is a property of some molecules and molecular complexes. A single molecule may give rise to a variety of polymorphs having distinct crystal structures and physical properties like melting point, thermal behaviors (e.g., measured by thermogravimetric analysis—"TGA", or differential scanning calorimetry—"DSC"), X-ray diffraction (XRPD) pattern, infrared absorption fingerprint, and solid state ($^{13}C$) NMR spectrum. One or more of these techniques may be used to distinguish different polymorphic forms of a compound.

Different salts and solid state forms (including solvated forms) of an active pharmaceutical ingredient may possess different properties. Such variations in the properties of different salts and solid state forms and solvates may provide a basis for improving formulation, for example, by facilitating better processing or handling characteristics, changing the dissolution profile in a favorable direction, or improving stability (polymorph as well as chemical stability) and shelf-life. These variations in the properties of different salts and solid state forms may also offer improvements to the final dosage form, for instance, if they serve to improve bioavailability. Different salts and solid state forms and solvates of an active pharmaceutical ingredient may also give rise to a variety of polymorphs or crystalline forms, which may in turn provide additional opportunities to assess variations in the properties and characteristics of a solid active pharmaceutical ingredient.

Discovering new solid state forms and solvates of a pharmaceutical product may yield materials having desirable processing properties, such as ease of handling, ease of processing, storage stability, and ease of purification or as desirable intermediate crystal forms that facilitate conversion to other polymorphic forms. New solid state forms of a pharmaceutically useful compound can also provide an opportunity to improve the performance characteristics of a pharmaceutical product. It enlarges the repertoire of materials that a formulation scientist has available for formulation optimization, for example by providing a product with different properties, e.g., a different crystal habit, higher crystallinity, or polymorphic stability, which may offer better processing or handling characteristics, improved dissolution profile, or improved shelf-life (chemical/physical stability). For at least these reasons, there is a need for additional solid state forms (including solvated forms) of Ponesimod.

SUMMARY OF THE DISCLOSURE

The present disclosure provides solid state forms or crystalline polymorphs of Ponesimod, processes for the preparation thereof, and pharmaceutical compositions thereof. In particular, the present disclosure relates to solid state forms of Ponesimod designated as Form T3 and Form T4 (defined herein).

The present disclosure provides any one of the above described polymorphs of Ponesimod and for use in the preparation of pharmaceutical compositions and/or formulations for use in medicine, preferably for the treatment of autoimmune diseases as described below, particularly multiple sclerosis (MS), such as relapsing MS, or relapse-remitting MS.

The present disclosure also encompasses the uses of any one of the above described polymorphs of Ponesimod of the present disclosure for the preparation of pharmaceutical compositions and/or formulations.

In another aspect, the present disclosure provides pharmaceutical compositions comprising any one of the above described solid state forms or crystalline polymorphs of Ponesimod according to the present disclosure.

In yet another embodiment, the present disclosure encompasses pharmaceutical formulations comprising any one of the above described solid state forms or crystalline polymorphs of Ponesimod and/or combinations thereof, or pharmaceutical compositions comprising any one of the above described solid state forms or crystalline polymorphs of Ponesimod and at least one pharmaceutically acceptable excipient.

The present disclosure comprises processes for preparing the above mentioned pharmaceutical compositions. The processes comprise combining any one of the above described solid state or crystalline polymorphs of Ponesimod and/or combinations thereof with at least one pharmaceutically acceptable excipient.

The solid state forms or crystalline polymorphs of Ponesimod as defined herein and the pharmaceutical compositions or formulations of the solid state forms or crystalline polymorphs of Ponesimod may be used as medicaments, particularly for the treatment of autoimmune diseases as described below, particularly multiple sclerosis (MS), such as relapsing MS, or relapse-remitting MS.

The present disclosure also provides methods of treating autoimmune diseases, comprising administering a therapeutically effective amount of any one of the solid state forms or crystalline polymorphs of Ponesimod of the present disclosure, or at least one of the above pharmaceutical compositions or formulations, to a subject suffering from autoimmune diseases as described below, particularly multiple sclerosis (MS), such as relapsing MS, or relapse-remitting MS, or otherwise in need of the treatment.

The present disclosure also provides the uses of any one of the solid state forms or crystalline polymorphs of Ponesimod of the present disclosure, or at least one of the above pharmaceutical compositions or formulations, for the manufacture of medicaments for treating autoimmune diseases as described below, particularly multiple sclerosis (MS), such as relapsing MS, or relapse-remitting MS.

According to any aspect or embodiment of the present disclosure autoimmune diseases preferably include those selected from the group consisting of: amyloidosis, ankylosing spondylitis, autoimmune hepatitis, autoimmune retinopathy, autoimmune urticaria, celiac disease, chronic inflammatory demyelinating polyneuropathy, Crohn's disease, endometriosis, fibromyalgia, Graves' disease, Guillain-Barre syndrome, interstitial cystitis, Kawasaki disease, lupus, Lyme disease, Meniere's disease, multiple sclerosis, myasthenia gravis, neutropenia, peripheral neuropathy, pernicious anemia, postmyocardial infarction syndrome, primary biliary cirrhosis, psoriasis, psoriatic arthritis, Raynaud's phenomenon, restless legs syndrome, rheumatic fever, rheumatoid arthritis, sarcoidosis, scleroderma, Type I diabetes, ulcerative colitis, uveitis, vasculitis, and vitiligo. Preferably the autoimmune disease is selected from the group consisting of multiple sclerosis (particularly relapsing-remitting multiple sclerosis) or psoriasis, and more preferably multiple sclerosis.

BRIEF DESCRIPTION OF THE DRAWINGS

FIG. 1 shows a characteristic X-ray powder diffraction pattern (XRPD) of Ponesimod Form T3.

FIG. 2 shows a characteristic XRPD of Ponesimod Form T4.

DETAILED DESCRIPTION OF THE DISCLOSURE

The present disclosure encompasses solid state forms or crystalline polymorphs of Ponesimod, processes for preparation thereof, and pharmaceutical compositions comprising at least one of, or a combination of these solid state forms. Solid state properties of Ponesimod and crystalline polymorph thereof can be influenced by controlling the conditions under which Ponesimod and crystalline polymorph thereof are obtained in solid form.

A solid state form (or polymorph) may be referred to herein as polymorphically pure or as substantially free of any other solid state (or polymorphic) forms. As used herein in this context, the expression "substantially free of any other forms" will be understood to mean that the solid state Form T3 or Form T4 contains about 20% (w/w) or less, about 10% (w/w) or less, about 5% (w/w) or less, about 2% (w/w) or less, about 1% (w/w) or less, or about 0% of any other forms of the subject compound as measured, for example, by XRPD. Thus, a solid state form or crystalline polymorph of Ponesimod described herein as substantially free of any other solid state forms would be understood to contain greater than about 80% (w/w), greater than about 90% (w/w), greater than about 95% (w/w), greater than about 98% (w/w), greater than about 99% (w/w), or about 100% (w/w) of the subject solid state form or crystalline polymorph of Ponesimod. In some embodiments of the disclosure, the described solid state form or crystalline polymorph of Ponesimod may contain from about 1% to about 20% (w/w), from about 5% to about 20% (w/w), or from about 5% to about 10% (w/w) of one or more other solid state form or crystalline polymorph of the same Ponesimod.

Depending on which other solid state forms or crystalline polymorphs a comparison is made, the solid state forms or crystalline polymorph of Ponesimod of the present disclosure has advantageous properties selected from at least one of the following: chemical purity, flowability, solubility, dissolution rate, morphology or crystal habit, stability—such as chemical stability as well as thermal and mechanical stability with respect to polymorphic conversion, stability towards dehydration and/or storage stability, low content of residual solvent, a lower degree of hygroscopicity, flowability, and advantageous processing and handling characteristics such as compressibility, and bulk density.

A solid state form, such as a crystal form or an amorphous form, may be referred to herein as being characterized by graphical data "as depicted in" or "as substantially depicted in" a Figure. Such data include, for example, powder X-ray diffractograms and solid state NMR spectra. As is well-known in the art, the graphical data potentially provides additional technical information to further define the respective solid state form (a so-called "fingerprint") which cannot necessarily be described by reference to numerical values or peak positions alone. In any event, the skilled person will understand that such graphical representations of data may be subject to small variations, e.g., in peak relative intensities and peak positions due to certain factors such as, but not limited to, variations in instrument response and variations in sample concentration and purity, which are well known to the skilled person. Nonetheless, the skilled person would readily be capable of comparing the graphical data in the Figures herein with graphical data generated for an unknown crystal form and confirm whether the two sets of graphical data are characterizing the same crystal form or two different crystal forms. A crystal form of Ponesimod referred to herein as being characterized by graphical data "as depicted in" or "as substantially depicted in" a Figure will thus be understood to include any crystal forms of Ponesimod characterized with the graphical data having such small variations, as are well known to the skilled person, in comparison with the Figure.

As used herein, and unless stated otherwise, the term "anhydrous" in relation to crystalline forms of Ponesimod, relates to a crystalline form of Ponesimod which does not include any crystalline water (or other solvents) in a defined, stoichiometric amount within the crystal. Moreover, an "anhydrous" form would typically not contain more than 1% (w/w), of either water or organic solvents as measured for example by TGA.

The term "solvate," as used herein and unless indicated otherwise, refers to a crystal form that incorporates a solvent in the crystal structure. When the solvent is water, the solvate is often referred to as a "hydrate." The solvent in a solvate may be present in either a stoichiometric or in a non-stoichiometric amount.

As used herein, and unless indicated otherwise, the term "wet crystalline form" refers to a polymorph that was not dried using any conventional techniques to remove residual solvent. Examples for such conventional techniques can be, but not limited to, evaporation, vacuum drying, oven drying, drying under nitrogen flow etc.

As used herein, and unless indicated otherwise, the term "dry crystalline form" refers to a polymorph that was dried using any conventional techniques to remove residual solvent. Examples for such conventional techniques can be, but not limited to, evaporation, vacuum drying, oven drying, drying under nitrogen flow etc.

As used herein, the term "isolated" in reference to crystalline polymorph of Ponesimod of the present disclosure corresponds to a crystalline polymorph of Ponesimod that is physically separated from the reaction mixture in which it is formed.

As used herein, unless stated otherwise, the XRPD measurements are taken using copper Kα radiation wavelength 1.5418 Å. XRPD peaks reported herein are measured using CuK α radiation, λ=1.5418 Å, at a temperature of 25±3° C.

As used herein, unless stated otherwise, 13C solid state NMR was measured on 400 MHz at room temperature at a spin rate of 11 kHz.

As used herein, unless stated otherwise, the DSC thermogram was measured by heating a sample at the temperature range 25-200° C. using heating rate 10° C./min.

A thing, e.g., a reaction mixture, may be characterized herein as being at, or allowed to come to "room temperature" or "ambient temperature", often abbreviated as "RT." This means that the temperature of the thing is close to, or the same as, that of the space, e.g., the room or fume hood, in which the thing is located. Typically, room temperature is from about 20° C. to about 30° C., or about 22° C. to about 27° C., or about 25° C.

The amount of solvent employed in a chemical process, e.g., a reaction or crystallization, may be referred to herein as a number of "volumes" or "vol" or "V." For example, a material may be referred to as being suspended in 10 volumes (or 10 vol or 10V) of a solvent. In this context, this expression would be understood to mean milliliters of the solvent per gram of the material being suspended, such that suspending a 5 grams of a material in 10 volumes of a solvent means that the solvent is used in an amount of 10 milliliters of the solvent per gram of the material that is being suspended or, in this example, 50 mL of the solvent. In another context, the term "v/v" may be used to indicate the number of volumes of a solvent that are added to a liquid mixture based on the volume of that mixture. For example, adding solvent X (1.5 v/v) to a 100 ml reaction mixture would indicate that 150 mL of solvent X was added.

A process or step may be referred to herein as being carried out "overnight." This refers to a time interval, e.g., for the process or step, that spans the time during the night, when that process or step may not be actively observed. This time interval is from about 8 to about 20 hours, or about 10-18 hours, typically about 16 hours.

As used herein, the term "reduced pressure" refers to a pressure that is less than atmospheric pressure. For example, reduced pressure is about 10 mbar to about 50 mbar.

As used herein and unless indicated otherwise, the term "ambient conditions" refer to atmospheric pressure and a temperature of 22-24° C.

The present disclosure comprises a crystalline polymorph of Ponesimod, designated Form T3.

The crystalline Form T3 of Ponesimod may be characterized by data selected from one or more of the following: an X-ray powder diffraction pattern substantially as depicted in FIG. 1; an X-ray powder diffraction pattern having peaks at 3.0, 6.0, 8.1, 9.2 and 13.3 degrees 2-theta±0.2 degrees 2-theta and missing peaks at 4.2, 6.8, 7.1, 11.7, 22.8 and 23.9 degrees 2-theta±0.2 degrees 2-theta; and combinations of these data.

Crystalline Form T3 of Ponesimod may be further characterized by an X-ray powder diffraction pattern having peaks at 3.0, 6.0, 8.1, 9.2 and 13.3 degrees 2-theta±0.2 degrees 2-theta and missing peaks at 4.2, 6.8, 7.1, 11.7, 22.8 and 23.9 degrees 2-theta±0.2 degrees 2-theta, and also having any one, two or three additional peaks at 10.6, 11.0 and/or 19.6 degrees 2-theta 0.2 degrees 2-theta.

Alternatively, crystalline Form T3 of Ponesimod may be characterized by an X-ray powder diffraction pattern having peaks at 3.0, 6.0, 8.1, 9.2, 11.0, and 13.3 degrees 2-theta±0.2 degrees 2-theta, or an X-ray powder diffraction pattern having peaks at 3.0, 6.0, 8.1, 9.2, 11.0, and 13.3 degrees 2-theta±0.2 degrees 2-theta, and an absence of peaks at 4.2, 6.8, 7.1, 11.7, 22.8 and 23.9 degrees 2-theta±0.2 degrees 2-theta. In either of these embodiments, the X-ray powder diffraction pattern may further include one or two additional peaks at 10.6 and/or 19.6 degrees 2-theta±0.2 degrees 2-theta.

Alternatively, crystalline Form T3 of Ponesimod may be characterized by an X-ray powder diffraction pattern having peaks at 3.0, 6.0, 8.1, 9.2, 10.6, 11.0, and 13.3 degrees 2-theta±0.2 degrees 2-theta, or an X-ray powder diffraction pattern having peaks at 3.0, 6.0, 8.1, 9.2, 10.6, 11.0, and 13.3 degrees 2-theta±0.2 degrees 2-theta, and an absence of peaks at 4.2, 6.8, 7.1, 11.7, 22.8 and 23.9 degrees 2-theta±0.2 degrees 2-theta. In either of these embodiments, the X-ray powder diffraction pattern may further include a peak at 19.6 degrees 2-theta±0.2 degrees 2-theta.

Crystalline Form T3 of Ponesimod may be characterized by each of the above characteristics alone/or by all possible combinations, e.g., an XRPD pattern having peaks at 3.0, 6.0, 8.1, 9.2, 10.6, 11.0, 13.3 and 19.6 degrees 2-theta±0.2 degrees 2-theta and missing peaks at 4.2, 6.8, 7.1, 11.7, 22.8 and 23.9 degrees 2-theta±0.2 degrees 2-theta; an XRPD pattern as depicted in FIG. 1, and combinations thereof.

In any aspect or embodiment of the present disclosure, crystalline Ponesimod Form T3 may be characterized as an anhydrous form.

In any aspect or embodiment of the present disclosure, Ponesimod Form T3 is polymorphically pure. Optionally, Ponesimod Form T3 may contain: about 20% (w/w) or less, about 10% (w/w) or less, about 5% (w/w) or less, about 2% (w/w) or less, about 1% (w/w) or less, about 0.5% (w/w) or less, or about 0% (i.e. undetectable levels) of any other solid state forms of the subject compound (i.e. Ponesimod) as measured, for example, by XRPD.

In any aspect or embodiment of the present disclosure, crystalline Form T3 of Ponesimod is isolated.

As discussed above, depending on which other solid state it is compared with, Ponesimod Form T3 according to the present disclosure may have advantageous properties as described above. Ponesimod Form T3 shows unexpected higher solubility, stability or other improved physical properties compared to other known crystalline polymorphs of Ponesimod.

The above Ponesimod Form T3 as described in any aspect or embodiment of the present disclosure can be prepared by a process including crystallization of Ponesimod in a solvent selected from: tetrahydrofuran (THF), isopropyl alcohol (IPA), ethanol, methyl tert-butylether (MTBE), or dichloromethane (DCM), optionally THF, or mixtures thereof, optionally isolating the Ponesimod Form T3, and optionally drying.

In embodiments, about 20 to about 80 vol, about 30 to about 60 vol, and in some embodiments about 50 vol of the solvent is used to dissolve Ponesimod. Preferably, the solvent is THF. The mixture may be heated to a temperature of: about 30° C. to about 70° C., about 40° C. to about 65° C., or about 60° C., preferably to form a solution, optionally with stirring.

The solution may be heated for about 5 to about 120 minutes, about 5 to about 30 minutes, and in embodiments about 10 minutes, optionally with stirring. The solution may be filtered.

Optionally, the Ponesimod Form T3 may be crystallized by solvent removal. In embodiments, the solvent removal is carried out by evaporation, in embodiments at: about 30° C. to about 70° C., about 50° C. to about 70° C., or about 60° C. under reduced pressure for about 30 to about 180 minutes, about 20 to about 120 minutes, and optionally about 45 to about 60 minutes. The solid is preferably allowed to cool to ambient temperature.

Optionally, Ponesimod Form T3 may be prepared by stirring a suspension comprising Ponesimod in methyl tert-butyl ether (MTBE). The MTBE may be used in an amount of: about 5 vol to about 40 vol, about 6 vol to about 20 vol, or about 8 vol to about 15 vol, or about 10 vol relative to Ponesimod. The stirring may be carried out at a temperature of: about 10° C. to about 100° C., about 15° C. to about 80° C., or about 20° C. about 60° C., about 20° C. to about 40° C., about 20° C. to about 30° C., or about 20° C. to about 25° C. The mixture may be stirred for any suitable time to prepare Form T3, preferably for about 12 hours to about 72 hours, about 18 hours to about 64 hours, about 12 hours to about 48 hours, or about 24 hours. The Form T3 may be isolated by any suitable method, such as by centrifuge, by decantation or by filtration, preferably by filtration. The Ponesimod starting material may be prepared by any suitable procedure. For example the Ponesimod may be prepared by reaction of (Z)-5-((Z)-3-chloro-4-hydroxybenzylidene)-2-(propylimino)-3-(o-tolyl)thiazolidin-4-one with (R)-3-chloropropane-1,2-diol optionally in the presence of a base (preferably an alkali metal hydroxide, more preferably sodium hydroxide or potassium hydroxide, and particularly potassium hydroxide) and a suitable solvent (preferably an alcohol, more preferably a $C_1$-$C_6$ alcohol, or a $C_1$-$C_3$ alcohol, and more particularly n-propanol). The reaction may be carried out at above ambient temperature (preferably at reflux, or at a temperature of about 30° C. to about 150° C., about 50° C. to about 130° C., about 60° C. to about 120° C., about 70° C. to about 110° C., or about 90° C. to about 100° C. The Ponesimod may be isolated from the reaction mixture by any suitable procedure, such as by one or more of distillation, extraction and trituration, using one more suitable solvents (alcohols—particularly $C_1$-$C_6$ alcohols or $C_1$-$C_3$ alcohols, and more particularly ethanol), ethers (particularly $C_4$-$C_8$ ethers or $C_4$-$C_6$ ethers, and more particularly methyl tert-butyl ether), and water, or mixtures thereof. Preferably, the Ponesimod is isolated from the reaction mixture by extraction. Prior to the extraction, the reaction mixture may be concentrated by distillation in order to reduce the volume to be extracted. The extraction may be carried out using a solvent comprising water, preferably a mixture of an organic solvent and water (preferably wherein the organic solvent is an alcohol, more preferably a $C_1$-$C_6$ alcohol, or a $C_1$-$C_3$ alcohol, and more particularly ethanol). The resulting Ponesimod may be used as a starting material for preparing Ponesimod Form T3 by stirring a suspension comprising Ponesimod in methyl tert-butyl ether (MTBE) as described above.

The present disclosure further includes a process for optimizing the particle size of Ponesimod Form T3, for example as prepared by the process as described in any aspect or embodiment of the disclosure. The process comprises suspending Ponesimod Form T3, preferably in MTBE (preferably about 3 vol to about 20 vol, about 4 vol to about 10 vol, or about 4 vol to about 8 vol, or about 5 vol, and stirred. The stirring may be carried out at a temperature of: about 20° C. to about 100° C., about 30° C. to about 80° C., or about 35° C. about 60° C., or about 45° C. to about 55° C. The stirring may be carried out over a period of about 30 minutes to about 4 hours, about 45 minutes to about 2 hours, or about 1 hour. The mixture may be cooled, preferably to a temperature of about 15° C. to about 35° C., about 20° C. to about 35° C., and the Form T3 may be optionally isolated. Optionally prior to isolating the Form T3, another portion of MTBE (preferably about 3 vol to about 20 vol, about 4 vol to about 10 vol, or about 4 vol to about 8 vol, or about 5 vol relative to Ponesimod) is added and the mixture further stirred at a temperature of: about 20° C. to about 40° C., about 20° C. to about 30° C., or about 20° C. to about 25° C., preferably for a period of: about 2 hours to about 12 hours, about 4 hours to about 10 hours, or about 6 hours to about 8 hours. The resulting Form T3 may be isolated by centrifuge, by decantation or by filtration, preferably by filtration.

Optionally, the isolated Form T3 may be further suspended in MTBE (preferably about 5 vol to about 40 vol, about 6 vol to about 20 vol, or about 8 vol to about 15 vol, or about 10 vol relative to Ponesimod), and stirred. The stirring may be carried out at a temperature of: about 20° C. to about 100° C., about 30° C. to about 80° C., or about 35° C. about 60° C., or about 45° C. to about 55° C. The stirring may be carried out over a period of about 30 minutes to about 4 hours, about 45 minutes to about 2 hours, or about 1 hour. The mixture may be cooled, preferably to a temperature of about 15° C. to about 35° C., about 20° C. to about 35° C., and the Form T3 may be optionally isolated by centrifuge, by decantation or by filtration, preferably by filtration. The Form T3 isolated at any stage in the herein described process be dried, preferably at elevated temperature (optionally at about 20° C. to about 80° C., about 30° C. to about 70° C., or about 35° C. about 60° C., or about 40° C. to about 50° C., preferably under vacuum or reduced pressure.

The above described processes for preparing Form T3 of Ponesimod may further comprise combining the Form T3 of Ponesimod with at least one pharmaceutically acceptable excipient to prepare a pharmaceutical formulation or dosage form.

The present disclosure comprises a solid state form or crystalline polymorph of Ponesimod, designated Form T4. The solid state form or crystalline Form T4 of Ponesimod may be characterized by data selected from one or more of the following: an X-ray powder diffraction pattern substantially as depicted in FIG. 2; an X-ray powder diffraction pattern having broad peaks at the range of 6.3, 13.3, 18.1 and 22.1 degrees 2-theta±0.3 degrees 2-theta, and combinations of these data. Crystalline T4 may be alternatively characterized by an X-ray powder diffraction pattern having broad peaks at: 5.0-8.8, 9.0-14.5, 15.0-19.0 and 20.0-30.0 degrees 2-theta±0.3 degrees 2-theta; or alternatively an X-ray powder diffraction pattern consisting of five broad peaks, wherein the peaks are at 3.0-4.8, 5.0-8.8, 9.0-14.5, 15.0-19.0 and 20.0-30.0 degrees 2-theta±0.3 degrees 2-theta. In any aspect or embodiment of this disclosure, crystalline Form T4 may be characterized by an onset melting peak at about 78° C.±5° C., at about 78° C.±2° C., at about 78° C.±1° C., or at about 78° C.±0.5° C., as measured by DSC. Crystalline form T4 of Ponesimod may be characterized by a combination of an X-ray powder diffraction pattern as described in any embodiment disclosed herein, in combination with an onset melting peak at about 78° C. as measured by DSC.

The solid state form or crystalline Form T4 of Ponesimod may be characterized by each of the above characteristics alone/or by all possible combinations, e.g., an XRPD pattern having broad peaks at the range of 6.3, 13.3, 18.1 and 22.1 degrees 2-theta±0.3 degrees 2-theta; an XRPD pattern as depicted in FIG. 2, and combinations thereof.

According to any aspect or embodiment of the present disclosure, Ponesimod Form T4 is preferably an anhydrous form. In another embodiment of the present disclosure, Ponesimod Form T4 is polymorphically pure. Optionally, according to any aspect or embodiment of the present disclosure, Ponesimod Form T4 may contain: about 20% (w/w) or less, about 10% (w/w) or less, about 5% (w/w) or less, about 2% (w/w) or less, about 1% (w/w) or less, about 0.5% (w/w) or less, or about 0% (i.e. undetectable levels) of any other solid state forms of the subject compound as measured, for example, by XRPD.

In one embodiment of the present disclosure, solid state form or crystalline Form T4 of Ponesimod is isolated.

The step of isolating Ponesimod or crystalline polymorphs of Ponesimod may be performed by crystallization.

Ponesimod Form T4 as described in any aspect or embodiment of the present disclosure can be prepared by a process comprising a solvent/antisolvent crystallization. In any aspect or embodiment of the process, Ponesimod Form T4 is prepared by crystallization from a mixture of a solvent and an antisolvent, wherein the solvent is selected from: cyclic ethers, preferably a $C_4$ to $C_7$ cyclic ether (more preferably a $C_4$-$C_5$ cyclic ether); or aliphatic monohydric alcohols (such as a $C_1$-$C_6$ monohydric alcohol, and preferably a $C_1$-$C_5$ monohydric alcohol) or combinations thereof. In any aspect or embodiment of the process the antisolvent is selected from: an aliphatic or cyclic alkane (preferably a $C_5$-$C_{10}$ aliphatic or cyclic alkane, more preferably a $C_5$-$C_8$ aliphatic or cyclic alkane), particularly cyclohexane, heptane, pentane, or water; or combinations thereof (typically cyclohexane), or the antisolvent may be water. In any aspect or embodiment, Ponesimod Form T4 may be prepared by crystallisation of Ponesimod from a mixture of a solvent and an antisolvent, wherein the solvent is selected from: a cyclic ether or an aliphatic monohydric alcohol or combinations thereof, and particularly wherein the solvent is a $C_4$-$C_7$ cyclic ether or a $C_1$-$C_5$ monohydric alcohol; and wherein the antisolvent is cyclohexane, heptane, pentane or water, and particularly cyclohexane). In any aspect or embodiment, Ponesimod Form T4 may be prepared by crystallisation of Ponesimod from a mixture of a solvent and an antisolvent, wherein the solvent is selected from the group consisting of: a $C_4$-$C_7$ or a $C_4$-$C_5$ cyclic ether or a $C_3$-$C_5$ aliphatic monohydric alcohol, or combinations thereof; and wherein the antisolvent is selected from: cyclohexane, heptane, pentane or water (particularly cyclohexane).

In any aspect or embodiment of the present invention, Ponesimod Form T4 can be prepared by a process comprising crystallization from a solvent which is tetrahydrofuran (TIF) or isopropyl alcohol (IPA) or a combination thereof, typically THF, and an antisolvent which is cyclohexane. In any aspect or embodiment of the present invention, Ponesimod Form T4 can be prepared by a process comprising crystallization from THE and cyclohexane.

According to any aspect or embodiment of the present disclosure, crystalline Form T4 may be prepared by a process comprising:

a) combining a solution of Ponesimod in a solvent (particularly cyclic ethers or aliphatic monohydric alcohols) or combinations thereof, with an antisolvent (particularly an aliphatic or cyclic alkane, or water);
b) optionally isolating the Ponesimod Form T4; and
c) optionally drying.

The solvent in step (a) may be a cyclic ether or an aliphatic monohydric alcohol, or a combination thereof, and the antisolvent is cyclohexane, heptane, pentane or water. According to any embodiment of the process, the solvent in step (a) is selected from the group consisting of: a $C_4$-$C_7$ or a $C_4$-$C_5$ cyclic ether or $C_1$-$C_7$ or a $C_3$-$C_5$ aliphatic monohydric alcohol; and the antisolvent is cyclohexane, heptane, pentane or water. In any embodiment of the process, the aliphatic monohydric alcohol in step a) is preferably selected from isopropyl alcohol, isobutanol and isoamyl alcohol, particularly isopropyl alcohol. The cyclic ether can be preferably selected from: THF, 2-methyl THE and 1,4-dioxane, and particularly THF. The aliphatic alkane can be preferably selected from cyclohexane, heptane, pentane or water. According to any embodiment of the process, the solvent in step (a) is preferably selected from THE or isopropanol; and the antisolvent is preferably selected from cyclohexane, heptane, pentane or water. Particularly, in step (a) the solvent is THF, and the antisolvent is cyclohexane.

In any aspect or embodiment of the process for preparing Ponesimod Form T4, the solvent is used an amount of about 3 vol to about 15 vol, about 3 vol to about 14 vol and preferably about 3 to 12 vol relative to Ponesimod. In any aspect or embodiment of the process for preparing Ponesimod Form T4: when the solvent is THF, the solvent may be used in an amount of about 2.5 vol to about 8 vol, about 3 to about 6 vol, about 3 to about 4 vol, or about 3.5 vol; when the solvent is IPA, the solvent may be used in the amount of 3 vol to about 10 vol, about 3 vol to about 6 vol, or about 4 vol, relative to Ponesimod. The antisolvent may be used in an amount of about 10 vol to about 60 vol, about 20 vol to about 50 vol and preferably about 30 to 40 vol relative to Ponesimod. When the antisolvent is cyclohexane, the antisolvent may be used in an amount of about 25 vol to about 50 vol, about 30 vol to about 45 vol, or about 35 vol relative to Ponesimod. The volume ratio of solvent to antisolvent in step (a) may be: about 1:2 to about 1:20, about 1:5 to about 1:15, about 1:6 to about 1:12, about 1:8 to about 1:12, and/or about 1:10. Particularly, when the solvent is THE and the antisolvent is cyclohexane, the volume ratio of THF to cyclohexane may be: about 1:5 to about 1:15, about 1:7 to about 1:12, about 1:8 to about 1:12 or about 1:10.

In any aspect or embodiment of the process for preparing Ponesimod Form T4, the mixture of Ponesimod in the solvent is preferably heated to a temperature of about 30° C. to about 60° C., in embodiments about 40° C. to about 60° C., and in other embodiments to about 45° C. to about 50° C., preferably with stirring. Optionally, the resulting solution may be filtered in order to remove undissolved particles. The filtration can be carried out at elevated temperature (such as the temperature of the mixture of Ponesimod in the solvent as described above) or at room temperature.

Step (a) may comprise addition of the antisolvent (e.g. cyclohexane, heptane, pentane or water, typically cyclohexane) to the solution of Ponesimod, or, preferably, the Ponesimod solution is added the antisolvent. In any embodiment of the process, step (a) may comprise adding Ponesimod solution to a pre-cooled antisolvent, wherein antisolvent is cooled to about 5 to about 15° C., about 6° C. to about 12° C., or about 8 to about 9° C. The addition may be carried out over a period of about 1 to about 30 minutes, about 1 to about 20 minutes, about 2 to about 10 or about 3 to about 8 minutes, or about 5 minutes.

Alternatively, the antisolvent (e.g. cyclohexane, heptane, pentane or water, typically cyclohexane) is added drop-wise into Ponesimod solution which is maintained at 0-5° C. The addition may be carried out over a period of about 2 to about 60 minutes, about 2 to about 45 minutes, and in some embodiments in about 5 minutes or about 30 to about 40 minutes, preferably with stirring.

According to any embodiment of the above processes for preparing Form T4, the reaction mixture comprising Ponesimod, solvent and antisolvent, may be maintained at about −4° C. to about 15° C., or about 0° C. to about 10° C., or about 0° C. to about 5° C. The mixture may be maintained at this temperature for about 0.5 to about 25 hours, about 1 to about 5 hours, about 2 to about 4 hours, or about 2.5 hours, preferably with stirring.

In any embodiment of the above processes for preparing Form T4, step (b) may include isolation of Ponesimod Form T4. The isolation may be carried out by any suitable means, such as by centrifuge, decantation, or by filtration, preferably by filtration. Preferably, the filtration is carried out at temperature of about 10° C. to about 40° C., preferably about 20° C. to about 30° C. Following the isolation, the product may be washed, and optionally dried. Drying may be done by nitrogen or air or under vacuum. Drying may be performed at a temperature of about 50° C. to about 70° C., in embodiment about 60° C. for about 4 to 48 hours, in embodiment 23 hours. When the drying is carried out under vacuum, a reduced pressure of: about 1 or about 200 mbar, about 1 to about 100 mbar, about 1 to about 50 mbar, and particularly about 5 to about 40 mbar or more particularly, about 20 mbar, may be used.

The above-described processes for preparing Form T4 of Ponesimod may further comprise combining the Form T4 of Ponesimod with at least one pharmaceutically acceptable excipient to prepare a pharmaceutical formulation or dosage form.

The above solid state forms or crystalline polymorphs can be used to prepare other solid state forms or crystalline polymorphs of Ponesimod.

The present disclosure provides any one or combination of the above described solid state forms or crystalline polymorphs of Ponesimod for use in the preparation of pharmaceutical compositions and/or formulations comprising Ponesimod and/or crystalline polymorphs thereof, and/or formulations for use in medicine, preferably for the treatment of autoimmune diseases as described above, particularly multiple sclerosis (MS), such as relapsing MS, or relapse-remitting MS.

The present disclosure also encompasses the use of any one or combination of the above described solid state form or crystalline polymorphs of Ponesimod of the present disclosure for the preparation of pharmaceutical compositions and/or formulations of solid state form or crystalline polymorph of Ponesimod, preferably for use in medicine, preferably for the treatment of autoimmune diseases as described above, particularly multiple sclerosis (MS), such as relapsing MS, or relapse-remitting MS.

The present disclosure comprises processes for preparing the above mentioned pharmaceutical compositions. The processes comprise combining any one of the above described solid state forms or crystalline polymorphs of Ponesimod of the present disclosure with at least one pharmaceutically acceptable excipient.

Pharmaceutical formulations of the present invention contain the solid state form of Ponesimod of the present invention, particularly crystalline Ponesimod Form T3 and Form T4. Thus in a preferred embodiment of the present disclosure, there is provided pharmaceutical formulations comprising one or more of the solid state Form T3 and/or Form T4 of Ponesimod as described in any aspect or embodiment disclosed herein. In addition to the active ingredient, the pharmaceutical formulations of the present invention can contain one or more excipients. Excipients are added to the formulation for a variety of purposes.

Diluents increase the bulk of a solid pharmaceutical composition, and can make a pharmaceutical dosage form containing the composition easier for the patient and caregiver to handle. Diluents for solid compositions include, for example, microcrystalline cellulose (e.g. Avicel®), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g. Eudragit®), potassium chloride, powdered cellulose, sodium chloride, sorbitol, and talc.

Solid pharmaceutical compositions that are compacted into a dosage form, such as a tablet, can include excipients whose functions include helping to bind the active ingredient and other excipients together after compression. Binders for solid pharmaceutical compositions include acacia, alginic acid, carbomer (e.g. carbopol), carboxymethylcellulose sodium, dextrin, ethyl cellulose, gelatin, guar gum, hydrogenated vegetable oil, hydroxyethyl cellulose, hydroxypropyl cellulose (e.g. Klucel®), hydroxypropyl methyl cellulose (e.g. Methocel®), liquid glucose, magnesium aluminum silicate, maltodextrin, methylcellulose, polymethacrylates, povidone (e.g. Kollidon®, Plasdone®), pregelatinized starch, sodium alginate, and starch.

The dissolution rate of a compacted solid pharmaceutical composition in the patient's stomach can be increased by the addition of a disintegrant to the composition. Disintegrants include alginic acid, carboxymethylcellulose calcium, carboxymethylcellulose sodium (e.g. Ac-Di-Sol®, Primellose®), colloidal silicon dioxide, croscarmellose sodium, crospovidone (e.g. Kollidon®, Polyplasdone®), guar gum, magnesium aluminum silicate, methyl cellulose, microcrystalline cellulose, polacrilin potassium, powdered cellulose, pregelatinized starch, sodium alginate, sodium starch glycolate (e.g. Explotab®), and starch.

Glidants can be added to improve the flowability of a non-compacted solid composition and to improve the accuracy of dosing. Excipients that can function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that can be included in the composition of the present invention include maltol, vanillin, ethyl vanillin, menthol, citric acid, fumaric acid, ethyl maltol, and tartaric acid.

Solid and liquid compositions can also be dyed using any pharmaceutically acceptable colorant to improve their appearance and/or facilitate patient identification of the product and unit dosage level.

In liquid pharmaceutical compositions of the present invention, Ponesimod and any other solid excipients are dissolved or suspended in a liquid carrier such as water, vegetable oil, alcohol, polyethylene glycol, propylene glycol, or glycerin.

Liquid pharmaceutical compositions can contain emulsifying agents to disperse uniformly throughout the composition an active ingredient or other excipient that is not soluble in the liquid carrier. Emulsifying agents that can be useful in liquid compositions of the present invention include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions of the present invention can also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as sorbitol, saccharin, sodium saccharin, sucrose, aspartame, fructose, mannitol, and invert sugar can be added to improve the taste.

Preservatives and chelating agents such as alcohol, sodium benzoate, butylated hydroxyl toluene, butylated hydroxyanisole, and ethylenediamine tetraacetic acid can be added at levels safe for ingestion to improve storage stability.

According to the present invention, a liquid composition can also contain a buffer such as gluconic acid, lactic acid, citric acid, or acetic acid, sodium gluconate, sodium lactate, sodium citrate, or sodium acetate. Selection of excipients and the amounts used can be readily determined by the formulation scientist based upon experience and consideration of standard procedures and reference works in the field.

The solid compositions of the present invention include powders, granulates, aggregates, and compacted compositions. The dosages include dosages suitable for oral, buccal, rectal, parenteral (including subcutaneous, intramuscular, and intravenous), inhalant, and ophthalmic administration. Although the most suitable administration in any given case will depend on the nature and severity of the condition being treated, the most preferred route of the present invention is oral. The dosages can be conveniently presented in unit dosage form and prepared by any of the methods well-known in the pharmaceutical arts.

Dosage forms include solid dosage forms like tablets, powders, capsules, suppositories, sachets, troches, and lozenges, as well as liquid syrups, suspensions, and elixirs.

The dosage form of the present invention can be a capsule containing the composition, preferably a powdered or granulated solid composition of the invention, within either a hard or soft shell. The shell can be made from gelatin and optionally contain a plasticizer such as glycerin and sorbitol, and an opacifying agent or colorant.

The active ingredient and excipients can be formulated into compositions and dosage forms according to methods known in the art.

A composition for tableting or capsule filling can be prepared by wet granulation. In wet granulation, some or all of the active ingredients and excipients in powder form are blended and then further mixed in the presence of a liquid, typically water, that causes the powders to clump into granules. The granulate is screened and/or milled, dried, and then screened and/or milled to the desired particle size. The granulate can then be tableted, or other excipients can be added prior to tableting, such as a glidant and/or a lubricant.

A tableting composition can be prepared conventionally by dry blending. For example, the blended composition of the actives and excipients can be compacted into a slug or a sheet and then comminuted into compacted granules. The compacted granules can subsequently be compressed into a tablet.

As an alternative to dry granulation, a blended composition can be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate, and colloidal silica. The proper use of these and other excipients in direct compression tableting is known to those in the art with experience and skill in particular formulation challenges of direct compression tableting.

A capsule filling of the present invention can comprise any of the aforementioned blends and granulates that were described with reference to tableting, but they are not subjected to a final tableting step.

A pharmaceutical formulation of Ponesimod can be administered. Ponesimod is preferably formulated for administration to a mammal, preferably a human, by injection. Ponesimod can be formulated, for example, as a viscous liquid solution or suspension, preferably a clear solution, for injection. The formulation can contain one or more solvents. A suitable solvent can be selected by considering the solvent's physical and chemical stability at various pH levels, viscosity (which would allow for syringeability), fluidity, boiling point, miscibility, and purity. Suitable solvents include alcohol USP, benzyl alcohol NF, benzyl benzoate USP, and Castor oil USP. Additional substances can be added to the formulation such as buffers, solubilizers, and antioxidants, among others. Ansel et al., Pharmaceutical Dosage Forms and Drug Delivery Systems, 7th ed.

The solid state forms or crystalline polymorphs of Ponesimod and the pharmaceutical compositions of Ponesimod of the present disclosure can be used as medicaments, particularly in the treatment of autoimmune diseases as described above, particularly multiple sclerosis (MS), such as relapsing MS, or relapse-remitting MS.

In another embodiment, Ponesimod Forms T3 and T4 and the pharmaceutical compositions of Ponesimod Forms T3 and T4 can be used as medicaments, particularly in the treatment of autoimmune diseases as described above, particularly multiple sclerosis (MS), such as relapsing MS, or relapse-remitting MS.

The present disclosure also provides methods of treating autoimmune diseases as described above, particularly multiple sclerosis (MS), such as relapsing MS, or relapse-remitting MS, comprising administering a therapeutically effective amount of a solid state form or crystalline polymorph of Ponesimod of the present disclosure, or at least one of the above pharmaceutical compositions, to a subject in need of the treatment.

Having thus described the disclosure with reference to particular preferred embodiments and illustrative examples, those in the art can appreciate modifications to the disclosure as described and illustrated that do not depart from the spirit and scope of the disclosure as disclosed in the specification. The Examples are set forth to aid in understanding the disclosure but are not intended to, and should not be construed to limit its scope in any way.

Powder X-Ray Diffraction (XRPD) Method

X-ray diffraction was performed on X-Ray powder diffractometer: Bruker D8 Advance; CuK radiation (λ=1.5418 Å); Lynx eye detector; laboratory temperature 22-25° C.; PMMA specimen holder ring. Prior to analysis, the samples were gently ground by means of mortar and pestle in order to obtain a fine powder. The ground sample was adjusted into a cavity of the sample holder and the surface of the sample was smoothed by means of a cover glass.

Measurement Parameters:

Scan range: 2-40 degrees 2-theta;

Scan mode: continuous;

Step size: 0.05 degrees;

Time per step: 0.5 s;

Sample spin: 30 rpm;

Sample holder: PMMA specimen holder ring.

Differential Scanning Calorimetry (DSC) Method

DSC was performed using TA instrument DSC Q-2000 differential scanning calorimetry. About 2-3 mg sample was accurately weighed into an aluminum pan, and covered with a lid having hole and then crimped. The sample cell was equilibrated at 25° C. and heated at a rate of 10° C./min up to 200° C. under the nitrogen atmosphere.

EXAMPLES

Ponesimod and (Z)-5-((Z)-3-chloro-4-hydroxybenzylidene)-2-(propylimino)-3-(o-tolyl)thiazolidin-4-one as used for the below examples can be prepared according to any procedure known from the literature. For example, Ponesimod used in example below can be prepared according to International Publication Publication Nos. WO 2010/046835, WO 2017/107972 and/or WO 2019/060147. (Z)-5-((Z)-3-chloro-4-hydroxybenzylidene)-2-(propylimino)-3-(o-tolyl)thiazolidin-4-one used for the examples below can be prepared according to International Publication No. WO2008/062376.

Example 1. Preparation of Ponesimod Form T3

Ponesimod (0.2 grams) was dissolved in 10 ml of tetrahydrofuran (THF) at 60° C. Filtered and clear solution was subjected to distillation on rotary evaporation under reduced pressure at 60° C. for 45-60 minutes. The flask was cooled down to 25° C. and the obtained solid was analyzed by XRPD and designated as Form T3 (FIG. 1).

Example 2. Preparation of Ponesimod Form T4

Ponesimod (2.0 grams) was dissolved in 7.0 ml of tetrahydrofuran at 45-50° C., filtered through 0.45 micron filter and clear solution was added into precooled cyclohexane (70 ml) at 8-9° C. under stirring. The reaction mixture was maintained at 0-5° C. for 2.5 hours, filtered and washed with cyclohexane (10 ml×3) and suck dried for 45 minutes. The sample was further dried under nitrogen atmosphere at 60° C. up to 23 hours and analyzed by XRPD to obtain Form T4 (FIG. 2).

Example 3. Preparation of Ponesimod Form T3

(Z)-5-((Z)-3-chloro-4-hydroxybenzylidene)-2-(propylimino)-3-(o-tolyl)thiazolidin-4-one (1.0 mole eq.), potassium hydroxide (1.5 mole eq.), (R)-3-chloropropane-1,2-diol (1.0 mole eq.) and n-propanol (10 V) were heated to 90-100° C. and kept under stirring till reaction complies to obtain Ponesimod. The solvent was distilled under vacuum till about 2-3 V remains in the reaction mixture and 6 V of Ethanol and 10 V of water were added to the reaction mass. The oily mass was separated, methyl tert butyl ether (MTBE, 10 V) was added and kept under stirring for 24 hours to obtain suspension. The suspension was filtered, washed with MTBE (2V×2) and suck dried to produce Form T3. In order to improve the yield and the rate of filtration, MTBE 5 V was added to the isolated solid, heated to 45-55° C. for 60 min and cooled to 20-30° C. to produce thick suspension. Additional MTBE (5 V) was added and kept at room temperature for 6-8 hours under stirring, filtering, washing with MTBE (2 V×2) and wet Form T3 was suck dried. Additional MTBE (10 V) was added to wet Form T3, heated to 45-55° C. for 60 minutes and cooled the suspension to 20-30° C. and kept for 6-8 hours to produce thick suspension separated by filtration, washing with MTBE (2 V×2) and drying under vacuum at 40-50° C. for 2 hours to obtain Form T3.

The invention claimed is:

1. A crystalline form of Ponesimod, designated as Form T3, which is characterized by data selected from:

(a) an X-ray powder diffraction pattern having peaks at 3.0, 6.0, 8.1, 9.2, 11.0, and 13.3 degrees 2-theta±0.2 degrees 2-theta; or (b) an X-ray powder diffraction pattern having peaks at 3.0, 6.0, 8.1, 9.2 and 13.3 degrees 2-theta±0.2 degrees 2-theta and missing peaks at 4.2, 6.8, 7.1, 11.7, 22.8 and 23.9 degrees 2-theta±0.2 degrees 2-theta.

2. The crystalline form according to claim 1, which is characterized by an X-ray powder diffraction pattern having peaks at 3.0, 6.0, 8.1, 9.2, 11.0, and 13.3 degrees 2-theta±0.2 degrees 2-theta, and an absence of peaks at 4.2, 6.8, 7.1, 11.7, 22.8 and 23.9 degrees 2-theta±0.2 degrees 2-theta.

3. The crystalline form according to claim 1, which is further characterized by an X-ray powder diffraction pattern having an additional peak at 10.6 degrees 2-theta±0.2 degrees 2-theta.

4. The crystalline form according to claim 1, which is further characterized by an X-ray powder diffraction pattern having an additional peak at 19.6 degrees 2-theta±0.2 degrees 2-theta.

5. The crystalline form according to claim 1, which is characterized by an X-ray powder diffraction pattern substantially as depicted in FIG. 1.

6. The crystalline form according to claim 1, which is an anhydrous form.

7. A crystalline form of Ponesimod, designated Form T4, which is characterized by data selected from:

(a) an X-ray powder diffraction pattern having broad peaks at the range of 6.3, 13.3, 18.1 and 22.1 degrees 2-theta±0.3 degrees 2-theta; or (b) an X-ray powder diffraction pattern having broad peaks at: 5.0-8.8, 9.0-14.5, 15.0-19.0 and 20.0-30.0 degrees 2-theta±0.3 degrees 2-theta.

8. The crystalline form according to claim 7, which is characterized by data selected from an X-ray powder diffraction pattern having 5 broad peaks at 3.0-4.8, 5.0-8.8, 9.0-14.5, 15.0-19.0 and 20.0-30.0 degrees 2-theta±0.3 degrees 2-theta.

9. The crystalline form according to claim 7, which is further characterized by an onset melting peak at about 78° C.±5° C., as measured by DSC.

10. The crystalline form according to claim 7, which is characterized by an X-ray powder diffraction pattern substantially as depicted in FIG. 2.

11. The crystalline form according to claim 1, which is isolated.

12. The crystalline form according to claim 1, which contains about 20% (w/w) or less of any other crystalline forms of Ponesimod.

13. The crystalline form according to claim 1, which contains about 20% (w/w) or less of an amorphous form of Ponesimod.

14. A pharmaceutical composition comprising the crystalline form according to claim 1.

15. A pharmaceutical formulation comprising the crystalline form according to claim 1, with at least one pharmaceutically acceptable excipient.

16. A process for preparing a pharmaceutical formulation comprising combining the crystalline form according to claim 1, with at least one pharmaceutically acceptable excipient.

17. A medicament comprising the crystalline form according to claim 1.

18. A method of treating an autoimmune disease selected from amyloidosis, ankylosing spondylitis, autoimmune hepatitis, autoimmune retinopathy, autoimmune urticaria, celiac disease, chronic inflammatory demyelinating polyneuropathy, Crohn's disease, endometriosis, fibromyalgia, Graves' disease, Guillain-Barre syndrome, interstitial cystitis, Kawasaki disease, lupus, Lyme disease, Meniere's disease, multiple sclerosis, myasthenia gravis, neutropenia, peripheral neuropathy, pernicious anemia, postmyocardial infarction syndrome, primary biliary cirrhosis, psoriasis, psoriatic arthritis, Raynaud's phenomenon, restless legs syndrome, rheumatic fever, rheumatoid arthritis, sarcoidosis, scleroderma, Type I diabetes, ulcerative colitis, uveitis, vasculitis, and vitiligo, comprising administering a therapeutically effective amount of the crystalline form according to claim 1 to a subject in need of the treatment.

19. A pharmaceutical composition comprising the crystalline form according to claim 7.

20. A pharmaceutical formulation comprising the crystalline form according to claim 7, with at least one pharmaceutically acceptable excipient.

21. A process for preparing a pharmaceutical formulation comprising combining the crystalline form according to claim 7, with at least one pharmaceutically acceptable excipient.

22. A medicament comprising the crystalline form according to claim 7.

23. A method of treating an autoimmune disease selected from amyloidosis, ankylosing spondylitis, autoimmune hepatitis, autoimmune retinopathy, autoimmune urticaria, celiac disease, chronic inflammatory demyelinating polyneuropathy, Crohn's disease, endometriosis, fibromyalgia, Graves' disease, Guillain-Barre syndrome, interstitial cystitis, Kawasaki disease, lupus, Lyme disease, Meniere's disease, multiple sclerosis, myasthenia gravis, neutropenia, peripheral neuropathy, pernicious anemia, postmyocardial infarction syndrome, primary biliary cirrhosis, psoriasis, psoriatic arthritis, Raynaud's phenomenon, restless legs syndrome, rheumatic fever, rheumatoid arthritis, sarcoidosis, scleroderma, Type I diabetes, ulcerative colitis, uveitis, vasculitis, and vitiligo, comprising administering a therapeutically effective amount of the crystalline form according to claim 7 to a subject in need of the treatment.

* * * * *